(12) United States Patent
Knutsson

(10) Patent No.: US 10,639,431 B2
(45) Date of Patent: May 5, 2020

(54) NEEDLE SHIELDING SYSTEM

(71) Applicant: Vigmed AB, Helsingborg (SE)

(72) Inventor: Per Knutsson, Helsingborg (SE)

(73) Assignee: Vigmed AB (SE)

( * ) Notice: Subject to any disclaimer, the term of this patent is extended or adjusted under 35 U.S.C. 154(b) by 88 days.

(21) Appl. No.: 15/750,727

(22) PCT Filed: Jul. 27, 2016

(86) PCT No.: PCT/SE2016/050731
§ 371 (c)(1),
(2) Date: Feb. 6, 2018

(87) PCT Pub. No.: WO2017/026938
PCT Pub. Date: Feb. 16, 2017

(65) Prior Publication Data
US 2019/0001074 A1    Jan. 3, 2019

(30) Foreign Application Priority Data

Aug. 7, 2015  (SE) ...................................... 1551060

(51) Int. Cl.
*A61M 5/00* (2006.01)
*A61M 25/00* (2006.01)
*A61M 5/32* (2006.01)

(52) U.S. Cl.
CPC ............ *A61M 5/3245* (2013.01); *A61M 5/32* (2013.01); *A61M 5/3273* (2013.01);
(Continued)

(58) Field of Classification Search
CPC .............. A61M 2005/325; A61M 5/32; A61M 5/3245; A61M 5/3273; A61M 5/3275
See application file for complete search history.

(56) References Cited

U.S. PATENT DOCUMENTS 4,846,811 A * 7/1989 Vanderhoof ........ A61M 5/3243
604/263
5,569,288 A * 10/1996 Yoon .................. A61B 10/0233
604/165.02
(Continued)

FOREIGN PATENT DOCUMENTS

DE        20218551 U1    4/2004
EP         1003588 A1    5/2000
(Continued)

OTHER PUBLICATIONS

International Search Report dated Apr. 8, 2019 related to corresponding application PCT/SE2016/050731.
(Continued)

*Primary Examiner* — Rebecca E Eisenberg
(74) *Attorney, Agent, or Firm* — Fishman Stewart PLLC

(57) ABSTRACT

Needle shielding systems are disclosed. The needle shielding system comprises a needle, a cover sleeve, and a needle shield. The needle has a needle tip and a needle bulge spaced apart from the needle tip. The cover sleeve is slidably mounted over the needle and comprises an end portion having an internal diameter smaller than the width of the needle bulge, and a cover sleeve shaft extending from the end portion towards the needle tip and having an internal diameter larger than the width of the needle bulge. The needle shield comprises a base plate slidably mounted over the needle adjacent to the end portion, and at least one resilient arm extending from the base plate towards the needle tip. In use the needle shield and cover sleeve move along the needle until the end portion contacts the needle bulge and the cover sleeve shaft and the arm cover the needle tip.

20 Claims, 4 Drawing Sheets

(52) U.S. Cl.
CPC ..... *A61M 5/3275* (2013.01); *A61M 2005/325* (2013.01); *A61M 2005/3246* (2013.01)

(56) References Cited

U.S. PATENT DOCUMENTS

| | | |
|---|---|---|
| 2003/0060774 A1 | 3/2003 | Woehr et al. |
| 2009/0312711 A1 | 12/2009 | Brimhall |
| 2012/0220956 A1 | 8/2012 | Kuracina et al. |
| 2013/0023835 A1* | 1/2013 | Kuracina ......... A61B 5/150633 604/263 |
| 2017/0361070 A1* | 12/2017 | Hivert .................. A61M 5/329 |

FOREIGN PATENT DOCUMENTS

| | | |
|---|---|---|
| EP | 2204204 A1 | 7/2010 |
| WO | 9908742 A1 | 2/1999 |
| WO | 2012139034 A1 | 10/2012 |
| WO | 2013187827 A1 | 12/2013 |
| WO | WO-2014/035970 A1 | 3/2014 |

OTHER PUBLICATIONS

International Search Report dated Oct. 14, 2016 related to corresponding application PCT/SE2016/050731.

* cited by examiner

NEEDLE SHIELDING SYSTEM

CROSS-REFERENCE TO RELATED APPLICATIONS

This application claims priority to the International Patent Application No. PCT/SE2016/050731, filed Jul. 27, 2016 which claims the benefit of Swedish Patent Application No. 1551060-5, filed Aug. 7, 2015, the contents of which are hereby incorporated by reference in its entirety.

TECHNICAL FIELD

The present disclosure relates to a needle shielding system including a cover sleeve for preventing accidental contact of a needle tip with an animal or human, such as patients and medical personnel.

BACKGROUND

The clinical utilization of a pointed hollow needle is well known in the medical art for the administration of solutions or suspensions, such as medicaments, to a human or animal. After puncturing of the skin and introduction of the needle tip the content of a syringe typically connected to the rear part of the needle is administered to the human or animal through the hollow needle. The needle has then done its duty and is withdrawn from the human or animal.

In recent years there has been great concern over the contamination of medical personnel with a patient's blood and recognition that blood contaminated sharps including used needles must be disposed of safely to avoid an accidental needle stick. This concern has arisen because of the advent of currently incurable and fatal diseases, such as Acquired Immunosuppressive Deficiency Syndrome ("AIDS"), hepatitis, etc., which can be transmitted by the exchange of body fluids from an infected person to another person.

Various needle shields have been developed to address the problem of accidental needlesticks by blood contaminated sharps. It is known to arrange needle tip shielding devices on an injection or infusion needle, said shielding device having the ability to snap in front of the needle tip upon withdrawal of the needle. These needle tip shielding devices have historically been manufactured in stainless steel. After the manufacturing and packing of the devices for infusion and injection, the devices are sterilized for hygienic reasons. An example of such a needle tip shielding device is disclosed in EP1003588.

However, needle tip shielding devices will, when being arranged in for example a catheter hub, scratch and tear the polymeric catheter hub lumen, resulting in a major risk of flushing plastic material into the blood stream of the patient. Additionally, the manufacturing of such shielding devices of stainless steel is cumbersome and costly, since several punching and bending stations have to be used. Additionally, due to the metal sheet of such device, there is a high risk of "drawer effect" on the needle shaft. A softer needle shielding device could be used to avoid such scratching. For instance, a plastic needle shield would not scratch the plastic of the catheter hub. However, the softer material characteristics of such a needle shield could also create the risk of it being able to slide over the stopper close to the needle tip and off the needle.

Swedish Patent Application No. 1451516-7 discloses a needle tip shielding device with a needle shield and a short tubular stopping body that alleviates the risk of "drawer effect". However, the small size of the tubular stopping body increases the manufacturing complexity of the device.

It would be desirable to provide an alternative needle shielding system which addresses the drawbacks associated with the above described needle tip shielding devices.

SUMMARY

The present disclosure seeks to mitigate, alleviate, circumvent or eliminate at least one of the above identified deficiencies in the art.

Accordingly an aspect disclosed herein relates to a needle shielding system comprising:
  a needle having a needle tip and a needle bulge spaced apart from the needle tip;
  a cover sleeve slidably mounted over the needle comprising:
    an end portion having an internal diameter smaller than the width of the needle bulge; and
    a cover sleeve shaft extending from the end portion towards the needle tip and having an internal diameter larger than the width of the needle bulge; and
  a needle shield comprising:
    a base plate slidably mounted over the needle adjacent to the end portion; and
    at least one resilient arm extending from the base plate towards the needle tip;
  wherein in use the needle shield and cover sleeve move along the needle until the end portion contacts the needle bulge and the cover sleeve shaft and the arm cover the needle tip.

Another aspect disclosed herein relates to a needle shielding system comprising:
  a needle having a needle tip and a needle bulge spaced apart from the needle tip; and
  a cover sleeve slidably mounted over the needle comprising:
    an end portion having a diameter smaller than the width of the needle bulge; and
    a cover sleeve shaft extending from the end portion towards the needle tip and having a diameter larger than the width of the needle bulge;
  wherein in use the cover sleeve moves along the needle until the end portion contacts the needle bulge and the cover sleeve shaft covers the needle tip.

Yet another aspect disclosed herein relates to a cover sleeve for shielding a needle comprising:
  an end portion adapted to contact the outer surface of the needle;
  an expanding portion adjacent to the end portion;
  a cover sleeve shaft adjacent to the expanding portion; and
  a flange adjacent to the cover sleeve shaft on the end of the sleeve opposing the end portion.

Further advantageous embodiments are disclosed below and in the appended patent claims.

BRIEF DESCRIPTION OF THE DRAWINGS

These and other aspects, features and advantages of which the disclosure is capable will be apparent and elucidated from the following description of non-limiting embodiments of the present disclosure, reference being made to the accompanying drawings, in which.

DETAILED DESCRIPTION

Embodiments of the present disclosure will be described in more detail below with reference to the accompanying figures in order for those skilled in the art to be able to carry out the disclosure. The disclosure may also be embodied in alternative forms and should not be construed as limited to the embodiments set forth herein. Rather, these embodiments are provided so that this disclosure will be thorough and complete, and will fully convey the scope of the disclosure to those skilled in the art. The disclosure is only limited by the appended patent claims.

Figure 1:
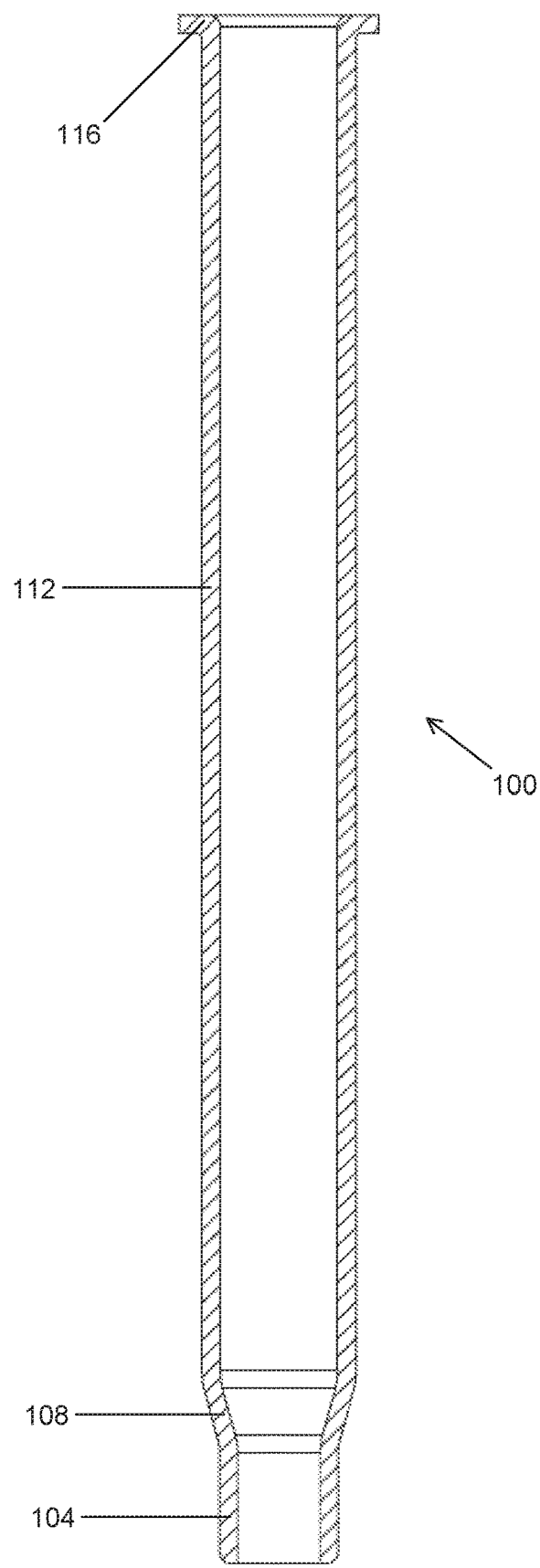
FIG. 1 is a cross-sectional view of a cover sleeve for use in a needle shielding system according to an embodiment of the present disclosure.
Figure 3:
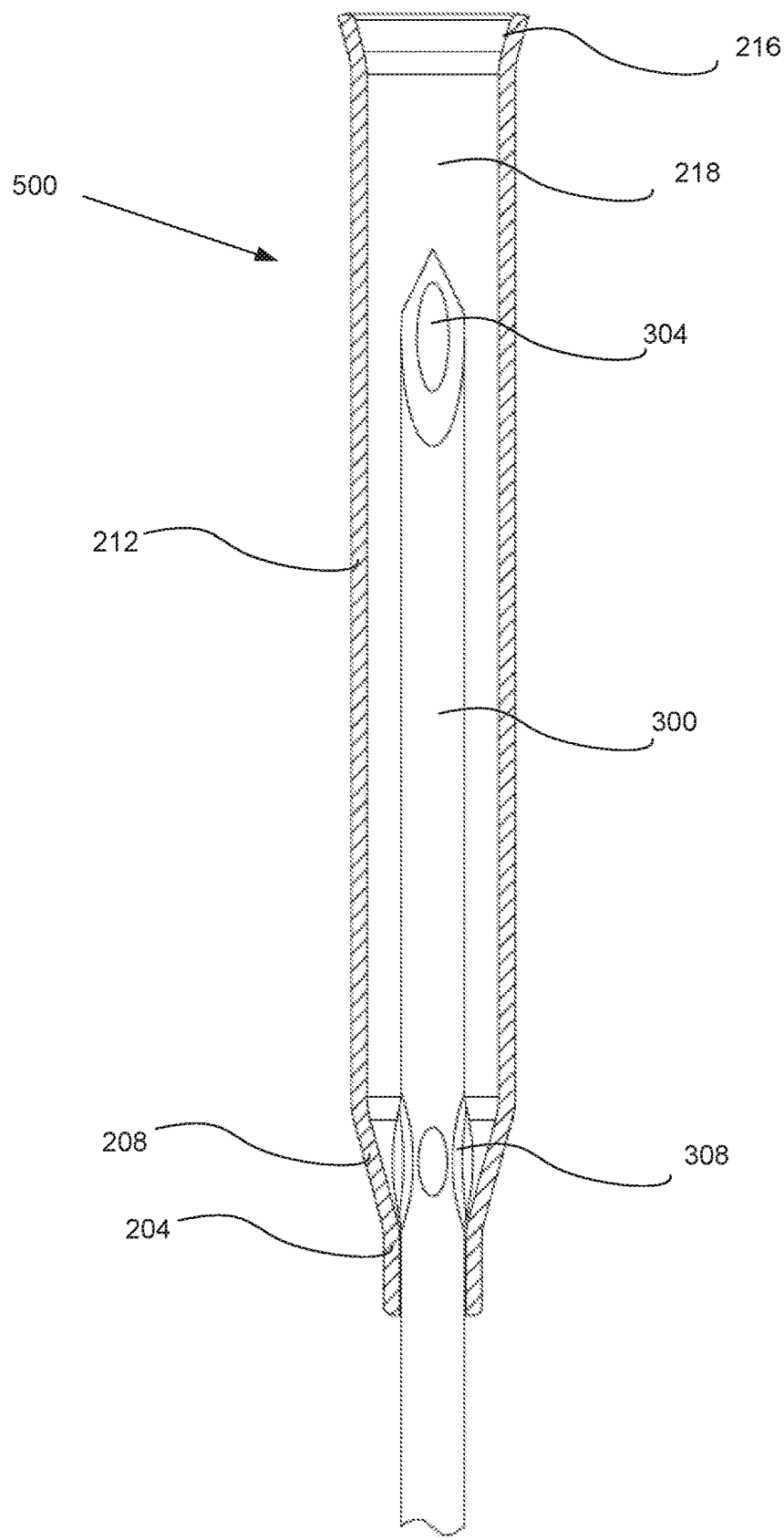
FIG. 3 is a partial cross-sectional view of a needle shielding system according to one embodiment of the present disclosure.
Figure 4:
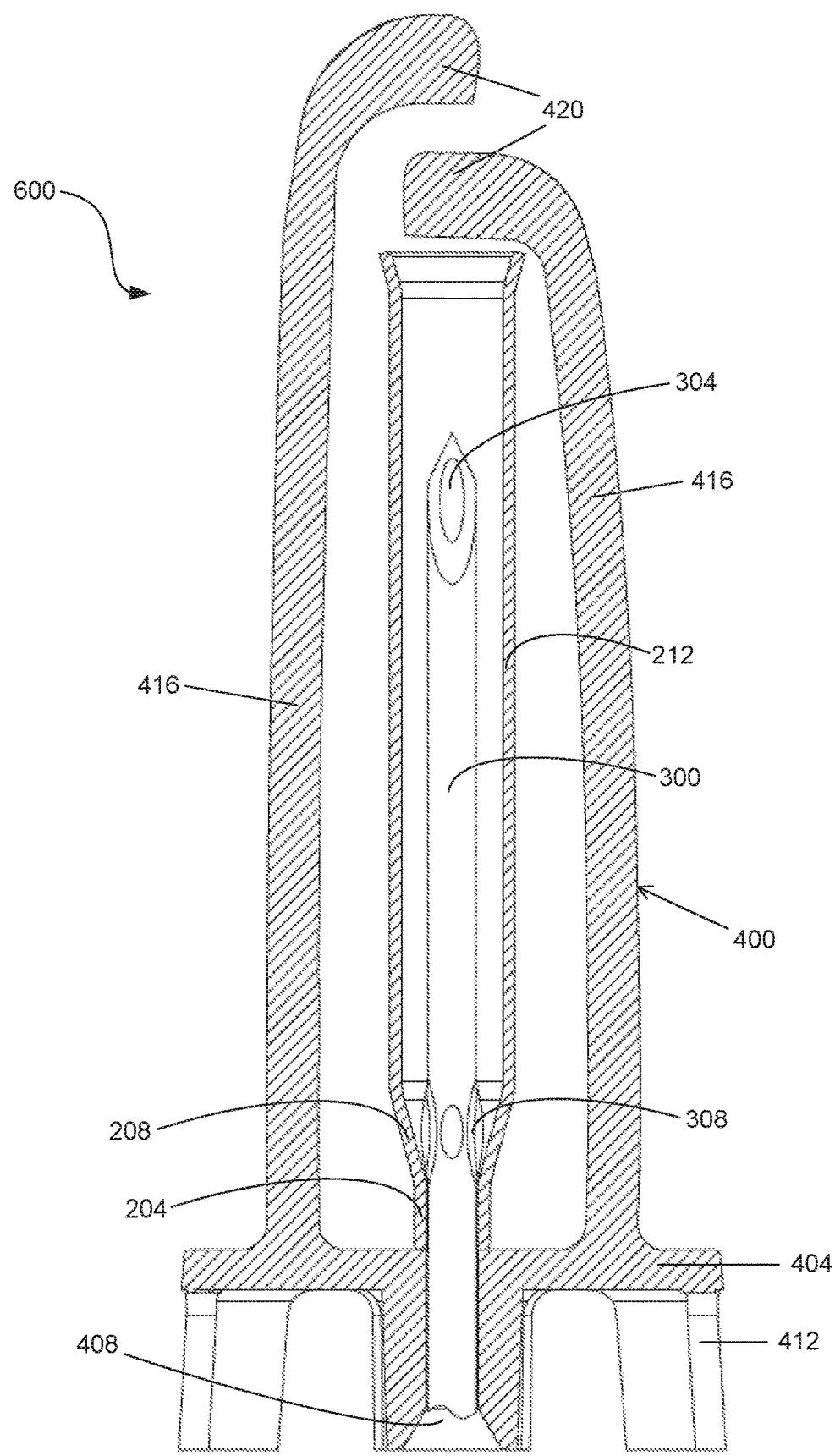
FIG. 4 is a partial cross-sectional view of a needle shielding system according to another embodiment of the present disclosure.

FIG. 1 illustrates a cover sleeve 100 for use in a needle shielding system. The sleeve 100 has a proximal end portion 104 which in use contacts a needle as will become apparent below when FIG. 3 and FIG. 4 are described. The internal diameter of end portion 104 is about 0.5 mm. The diameter of the cover sleeve 100 widens distally through expanding portion 108 located adjacent to end portion 104. In use expanding portion 108 accommodates a needle bulge on the needle. Again, this will become apparent from the description below. The sleeve 100 also has a cover sleeve shaft 112 adjacent to the expanding portion 108. Shaft 112 is significantly longer than both end portion 104 and expanding portion 108 and may be arranged so that it does not contact the needle in use due to its larger internal diameter relative to end portion 104. A flange 116 is located adjacent to shaft 112 and on the distal end zone of the sleeve 100 opposing proximal end portion 104.

Figure 2:
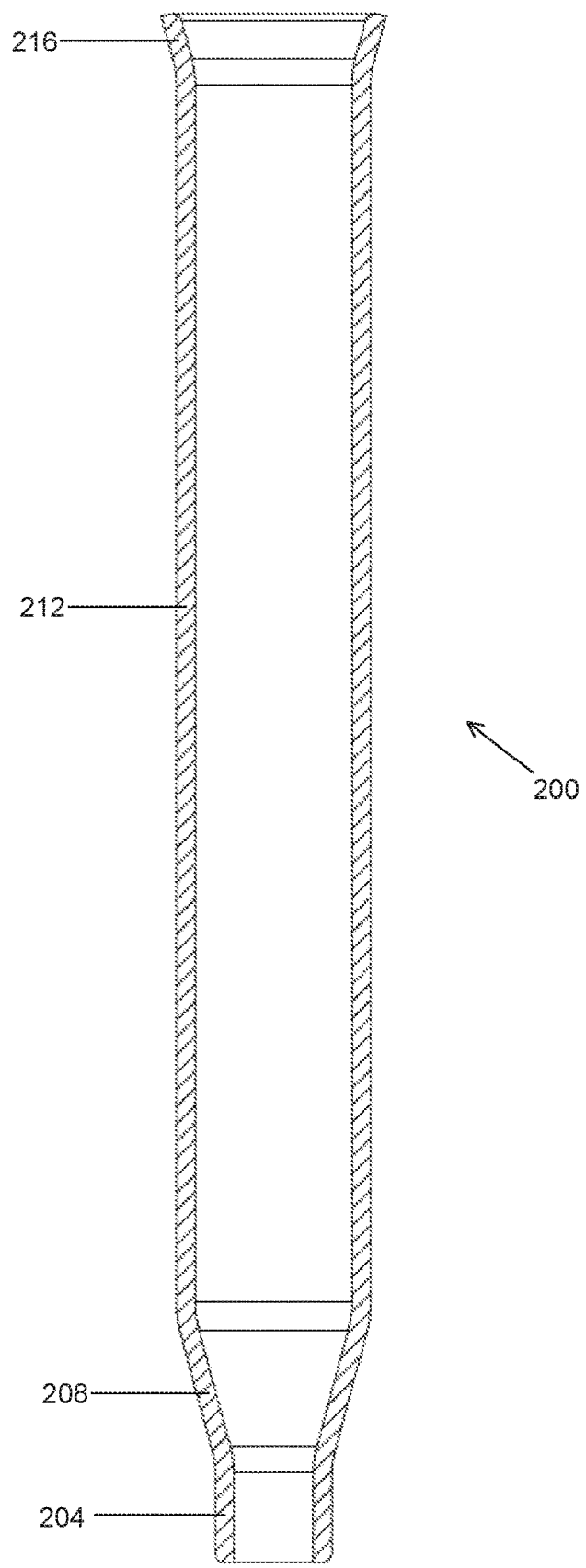
FIG. 2 is a cross-sectional view of a cover sleeve for use in a needle shielding system according to another embodiment of the present disclosure.

FIG. 2 illustrates an alternative cover sleeve 200 that is similar in structure to cover sleeve 100. Sleeve 200 has a proximal end portion 204 with an internal diameter of about 0.5 mm and an expanding portion 208 located adjacent to and distally of end portion 204. A cover sleeve shaft 212 is located adjacent to and distally of the expanding portion 208. Shaft 212 may be arranged so that it does not contact a needle in use. Shaft 212 has a larger internal diameter than end portion 204 and does not contact the needle during use. A conical flange 216 is located adjacent to shaft 212 and on the distal end of the sleeve 200 opposing proximal end portion 204.

Flange 116 and conical flange 216 impart additional strength to the cover sleeves 100, 200. Conical flange 216 allows for improved capture of fluid drops within the sleeve 200 that may be present on the needle after withdrawal from the patient. The flanges also provide an additional stopping mechanism between a needle bulge on the needle and the front of the cover sleeves 100, 200. Perhaps most importantly, flanges 116, 216 realize an improved industrial assembling of a needle shielding system, since the flanges 116, 216 allow for correct positioning of the cover sleeves 100, 200 in a feeding chute in an automated manufacturing process.

The contact between end portions 104, 204 and the surface of the needle shaft guides the cover sleeves 100, 200 during axial movement along the needle to ensure other parts of the sleeve (e.g. shafts 112, 212 and flanges 116, 216) do not scratch or scrape against the surface of the needle. In this way shelving effect may be avoided. The axial extension of the end portions 104, 204 may for this purpose be at least 0.5 mm. For positioning the needle aligned and centrally of the sleeve 100, 200, such that the needle does not come in contact with the sleeve 100, 200 distally of the needle bulge 108, another factor, in addition to the axial extension of the end portion 104, 204, is the tolerance play between the needle and the sleeve 100, 200. For a thin needle the manufacturing tolerance for its outer diameter is 0.41±0.005 mm and the manufacturing tolerance of the inner diameter of the end portion 104, 204 is 0.43±0.01 mm. This gives a maximum play of 0.0175 mm (if the inner diameter of end portion 104, 204 is 0.44 mm and the outer diameter of the needle is 0.405 mm). With this play there is a need for an axial extension of the end portion 104, 204 of 0.5 mm.

A needle shielding system 500 is depicted in FIG. 3. System 500 comprises a cover sleeve 200 and a needle 300. Needle 300 has a needle tip 304 and a needle bulge 308 located on the shaft of the needle away from the needle tip. Prior to use the cover sleeve 200 is slidably mounted on the needle 300 and remains away from the needle tip 304 and needle bulge 308 further down the needle shaft towards the end of the needle closest to the medical personnel (not shown). The internal surface of the end portion 204 is always in direct contact with the outer surface of the needle shaft. After medical personnel have inserted the needle into a patient and injected a medicament, the needle is withdrawn from the patient and the cover sleeve 200 is moved along the needle shaft towards the patient so that conical flange 216 and sleeve shaft 212 pass over the needle bulge 308. Flange 216 also passes over needle tip 304, such that the needle tip 304 and/or the front distal zone of the needle are contained in a sleeve compartment 218. In this way, the part of the needle being in contact with blood when inserting for example an intravenous catheter into a vein may be isolated from the surroundings, such that it may not be accidentally contacted. The sleeve compartment 218 also acts as a blood collection chamber, since blood splash from the needle tip will be caught by this sleeve compartment 218. Movement of sleeve 200 is continued until end portion 204 contacts needle bulge 308 as shown in FIG. 3. The cover sleeve 200 can then move no further along the needle shaft as the needle bulge 308 has a width wider than the internal diameter of the end portion 204. The needle bulge is housed in expanding portion 208. In the position shown in FIG. 3, the needle tip 304 is enclosed within the cover sleeve shaft 212 thereby protecting medical personnel from accidental contact with the needle tip, as mentioned above. A person skilled in the art will understand that cover sleeve 100 shown in FIG. 1 is equally capable of replacing cover sleeve 200 in the interaction with the needle 300 as described in FIG. 3.

An alternative needle shielding system 600 is illustrated in FIG. 4. The system 600 comprises a cover sleeve 200, a needle 300, and a needle shield 400. Again, cover sleeve 100 could be used in place of cover sleeve 200 as shown in FIG. 4. Needle shield 400 has a base plate 404 with a hole 408 for receiving the needle 300 through the centre of the plate. The base plate 404 also has at least one tongue 412 on the periphery of the plate. The tongues 412 facilitate connection of the needle shield 400 to a catheter hub or syringe by exercising a force on the inner walls of the catheter hub (not shown). A plurality of tongues 412 may be evenly spread around the periphery of the base plate 404. Two resilient arms 416 extend away from the base plate 404 in the same general direction as the longitudinal axis of the needle 300. Each arm 416 ends in hooked tip 420. FIG. 4 shows the resilient arms 416 in a resting state in which the needle 300 is enclosed within the needle shield 400. The hooked tips 420 and the arms 416 may be urged apart from each other into a tension state (not shown) in which free passage of the needle 300 is possible through hole 408 and the hooked tips 420 are in contact with the surface of the needle 300.

Prior to use the cover sleeve 200 is mounted on the needle 300 away from the needle tip 304 in the same manner as described above with respect to the needle shielding system 500 shown in FIG. 3. The needle shield 400 is then mounted on the needle 300 through the hole 408 and over the cover sleeve 200 so that the cover sleeve 200 is located between the arms 416 and the needle shield 400 is in the tension state referred to above. After injection of a medicament and withdrawal of the needle from the patient, the needle shield 400 is moved along the needle shaft towards the patient. The base plate 404 contacts the end portion 204 of the cover sleeve 200 so that the cover sleeve 200 moves simultaneously with the needle shield 400. When the hooked tips 420 pass over the needle tip 304 the arms 416 snap centrally in front of the needle tip. The end portion 204 then contacts needle bulge 308 and the cover sleeve 200 and needle shield 400 can then move no further along the needle shaft.

Use of cover sleeves 100, 200 in conjunction with the needle shield 400 results in the entire needle sharp area being covered, i.e. the shaft is covered from the front of the needle tip 304, such as distally beyond the needle tip 304, all the way down to the needle bulge 308, thus protecting medical personnel from accidental contact with the needle tip, the side of the needle shaft, and biological fluids on the needle. Moreover, splatter of blood or other biological fluid is minimized as the blood that is around the needle sharp area is contained within the sleeve shafts 112, 212 after withdrawal of the needle from the patient. The design of the sleeves 100, 200 avoids manufacturing difficulties associated with shorter stoppers and allows for higher mounting rate and more secure fit on injection needles, IV cannulae, and other IV catheter systems.

The cover sleeves 100, 200 are preferably made from metal, such as stainless steel. A polymer body has a lower modulus of elasticity (polymer (PC) 2300 MPa or (LCP) 7000 MPa) compared to the modulus of elasticity of metal (210 000 MPa). Thus the resistance to being deformed elastically is very high when both the needle 300 and the cover sleeves 100, 200 are made of metal. This makes it extremely hard to push the cover sleeves 100, 200 over and beyond the needle bulge 308 and is desirable given that the needle 300 should have a small diameter and that the needle bulge 308 be made as small as possible.

Further, the larger outer diameter of the cover sleeves 100, 200 compared to the outer diameter of the needle 300 makes it much harder for the needle shield 400 to transverse past the cover sleeves 100, 200.

The needle shield 400 may be made of a plastic material. The plastic material will have a suitable combination of tenacity, rigidity, fatigue resistance, elasticity, and creep deformation resistance. A suitable plastic material has a high creep deformation resistance, i.e. it has a low tendency to slowly move or deform permanently under the influence of an applied external pressure. Hence, needle shield 400 may be stored in an assembled ready mode (tension state) for a prolonged time without extensive creep deformation of the arms 416 or the tongues 412. A plastic needle shield 400 may be colored for ease of recognition. The needle shield 400 may be a monolithic homogenous injection molded plastic needle shield. An advantage of a monolithic needle shield 400 is a lower production cost in comparison to other devices made of more than one part requiring subsequent assembly. The needle shield 400 may be made of a thermoplastic polymer. The thermoplastic polymer could be crystalline, amorphous, or comprising crystalline and amorphous alternating regions. A creep resistance of the thermoplastic polymer of choice may be at least 1200 MPa (ISO 527, ASTM D638). Suitable plastics for the needle shield 400 may be selected from the group comprising of polyoxymethylene (POM), polybutylen terephthalate (PBTP), polymethyl methacrylate (PMMA), acrylonitrile butadiene styrene (ABS), styrene acrylonitrile (SAN), acrylonitrile styrene acrylate (ASA), polystyrene (PS), styrene butadiene (SB), liquid crystal polymer (LCP), polyamide (PA), polysulfone (PSU), polyetherimide (PEI), polycarbonate (PC), polyphenylene oxide (PPO), and/or PPO/SB, and co- and terpolymers thereof. These polymers have the advantages of providing enhanced storing capacity, even in a strained state, due to the excellent structure memory of these polymers.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality, and instead includes a both a singularity and a plurality. Reference signs in the claims are provided merely as a clarifying example and shall not be construed as limiting the scope of the claims in any way.

The invention claimed is:

1. A needle shielding system comprising:
   a needle having a needle tip and a needle bulge spaced apart from the needle tip;
   a cover sleeve slidably mounted over the needle comprising:
   a proximal end portion having an internal diameter smaller than the width of the needle bulge, wherein an axial extension of the proximal end portion is at least 0.5 mm; and
   a cover sleeve shaft having a longitudinal length extending distally from the proximal end portion towards the needle tip, and having an internal diameter larger than a width of the needle bulge; and
   a needle shield including:
   a base plate slidably mounted over the needle adjacent to the proximal end portion; and
   at least one resilient arm extending distally from the base plate towards the needle tip;
   wherein the at least one resilient arm includes first and second arms configured to span an entirety of the longitudinal length of the cover sleeve shaft while the first and second arms are substantially parallel to each other; and
   wherein in use the needle shield and cover sleeve are adapted to move along the needle until the proximal end portion contacts the needle bulge and the cover sleeve shaft and the arm cover the needle tip.

2. The system according to claim 1, wherein the cover sleeve further comprises an expanding portion between the proximal end portion and the cover sleeve shaft.

3. The system according to claim 1, wherein the cover sleeve further comprises a flange or a conical flange adjacent to the cover sleeve shaft on an end of the sleeve opposing the proximal end portion.

4. The system according to claim 1, wherein the cover sleeve has an expanding portion that widens distally to receive the needle budge and includes stainless steel.

5. The system according to claim 1, wherein the first and second arms of the needle shield are resilient arms.

6. The system according to claim 1, wherein the at least one resilient arm includes an end with a hooked tip.

7. The system according to claim 1, wherein the base plate has a hole for receiving the needle through a central area of the base plate.

8. The system according to claim 1, wherein the base plate includes at least one tongue on a periphery of the plate.

9. The system according to claim 1, further comprising a plurality of tongues distributed around a periphery of the base plate, and each of the plurality of tongues extending relative to a longitudinal axis of the needle.

10. The system according to claim 1, wherein the needle shield includes plastic.

11. The system according to claim 1, wherein the first and second arms include respective first and second hooked tips on opposing sides of a longitudinal space therebetween.

12. A needle shielding system comprising:
a needle having a needle tip and a needle bulge spaced apart from the needle tip; and
a cover sleeve slidably mounted over the needle comprising:
an end portion having a diameter smaller than the width of the needle bulge, wherein the axial extension of the end portion is at least 0.5 mm; and
a cover sleeve shaft having a longitudinal length extending from the end portion towards the needle tip and having a diameter larger than the width of the needle bulge; and
first and second arms configured to span an entirety of the longitudinal length of the cover sleeve shaft while the first and second arms are substantially parallel to each other,
wherein in use the cover sleeve is adapted to move along the needle until the end portion contacts the needle bulge and the cover sleeve shaft covers the needle tip.

13. The system according to claim 12, wherein the cover sleeve further comprises an expanding portion between the end portion and the cover sleeve shaft.

14. The system according to claim 12, wherein the end portion includes a proximal end portion having the axial extension to resist scratching of the cover sleeve shaft against the needle, and the cover sleeve further comprises an expanding portion between the end portion and the cover sleeve shaft.

15. The system according to claim 12, wherein the cover sleeve further comprises a flange or a conical flange adjacent to the cover sleeve shaft on the end of the sleeve opposing the end portion.

16. The needle shielding system according to claim 12, wherein the first and second arms include respective first and second hooked tips on opposing sides of a longitudinal space therebetween.

17. The needle shielding system according to claim 12, further comprising a base plate having a periphery that includes a plurality of tongues distributed thereon.

18. A cover sleeve for shielding a needle comprising:
an end portion adapted to contact the outer surface of the needle, wherein an axial extension of the end portion is at least 0.5 mm;
an expanding portion adjacent to the end portion;
a cover sleeve shaft having a longitudinal length and being adjacent to the expanding portion;
first and second arms configured to span an entirety of the longitudinal length of the cover sleeve shaft while the first and second arms are substantially parallel to each other; and
a flange adjacent to the cover sleeve shaft on an end of the sleeve opposing the end portion.

19. The cover sleeve according to claim 18, wherein the first and second arms include respective first and second hooked tips on opposing sides of a longitudinal space therebetween.

20. The cover sleeve according to claim 18, further comprising a base plate having a periphery that includes a plurality of tongues distributed thereon.

* * * * *